(12) United States Patent
Filho

(10) Patent No.: US 11,471,186 B2
(45) Date of Patent: Oct. 18, 2022

(54) THIN CANNULAS TROCAR AND METHOD

(71) Applicant: Luiz Lanat Pedreira de Cerqueira Filho, Orlando, FL (US)

(72) Inventor: Luiz Lanat Pedreira de Cerqueira Filho, Orlando, FL (US)

(73) Assignee: Luiz Lanat Pedreira de Cerqueira Filho, Orlando, FL (US)

( * ) Notice: Subject to any disclaimer, the term of this patent is extended or adjusted under 35 U.S.C. 154(b) by 353 days.

(21) Appl. No.: 16/424,449

(22) Filed: May 28, 2019

(65) Prior Publication Data

US 2020/0015846 A1    Jan. 16, 2020

Related U.S. Application Data

(60) Provisional application No. 62/789,515, filed on Jan. 7, 2019, provisional application No. 62/690,822, filed on Jun. 27, 2018.

(51) Int. Cl.
| | |
|---|---|
| *A61B 17/34* | (2006.01) |
| *A61B 17/02* | (2006.01) |
| *A61B 90/00* | (2016.01) |
| *A61B 34/30* | (2016.01) |

(52) U.S. Cl.
CPC ...... *A61B 17/3421* (2013.01); *A61B 17/0218* (2013.01); *A61B 17/3462* (2013.01); *A61B 34/30* (2016.02); *A61B 90/361* (2016.02); *A61B 90/37* (2016.02); *A61B 2017/3445* (2013.01)

(58) Field of Classification Search
CPC ..... A61B 17/02; A61B 17/0218; A61B 17/34; A61B 17/3463; A61B 17/3421
See application file for complete search history.

(56) References Cited

U.S. PATENT DOCUMENTS

| | | | | |
|---|---|---|---|---|
| 6,217,555 | B1* | 4/2001 | Hart | A61B 17/3462 |
| | | | | 128/DIG. 26 |
| 9,028,483 | B2* | 5/2015 | Long | A61B 18/1402 |
| | | | | 606/41 |
| 9,687,271 | B2* | 6/2017 | Norton | A61B 17/0218 |
| 9,775,642 | B2* | 10/2017 | Azarbarzin | A61B 17/3421 |
| 10,492,825 | B2* | 12/2019 | Lambrecht | A61B 17/3462 |
| 2005/0070851 | A1* | 3/2005 | Thompson | A61B 17/3462 |
| | | | | 604/167.03 |
| 2011/0152859 | A1* | 6/2011 | Long | A61B 18/1402 |
| | | | | 606/41 |
| 2011/0295077 | A1* | 12/2011 | Stefanchik | A61B 17/0293 |
| | | | | 600/210 |

(Continued)

*Primary Examiner* — Christopher J Beccia

(57) ABSTRACT

An invention for transfixing a plurality of cannulas 14 through a tissue 25 for providing a plurality of entry-ports 33 to a surgical site 26, comprising: a base 10; and a plurality of cannulas 14 connected to said base 10; wherein each said cannula 14 includes an access-port 3, is provided. Also, the invention for transfixing a plurality of cannulas 14 through a tissue 25 for providing a plurality of entry-ports 33 to a surgical site 26, comprising: a sleeve 9 including a base 10; said sleeve 9 including a plurality of cannulas 14 connected to said base 10; a mandrel 1 including a handle 7; and said mandrel 1 including a plurality of piercing tips 2 connected to said handle 7; wherein said mandrel 1 detachably engage said sleeve 9 forming a single punch assembly; wherein said cannula 14 includes an access-port 3 to a surgical site 26, is provided.

18 Claims, 15 Drawing Sheets

(56) References Cited

U.S. PATENT DOCUMENTS

2014/0276464 A1* 9/2014 Lambrecht ......... A61B 17/3498
604/256
2014/0288377 A1* 9/2014 Worrel ............... A61B 17/3431
600/208

* cited by examiner

THIN CANNULAS TROCAR AND METHOD

CROSS-REFERENCE TO RELATED APPLICATIONS

This application claims an invention which was disclosed in provisional application number U.S. 62/690,822 filed 2018 Jun. 27, entitled "Thin cannulas trocar", and in application number U.S. 62/789,515 filed 2019 Jan. 7, entitled "Thin cannulas trocar and method." The benefit under 35 USC § 119(e) of the United States provisional application is hereby claimed, and the afore mentioned application is hereby incorporated herein by reference.

DESCRIPTION

Field of Invention

The invention is in the field of medical devices and pertain, particularly, to a trocar 34 for transfixing a plurality of cannula 14 in a tissue 25 to provide a plurality entry-port 33 to a surgical site 26.

BACKGROUND

In the art of trocars for perform access passages in a tissue 25 for a surgical site 26, many different types of trocars have been developed as a portal for performing video surgery. One problem with the traditional trocars 39 is to have a single cannula with thick outer diameter that damages the tissue 25. Another limitation of the traditional trocar 39 is the need for an incision in the tissue 25 generally with the use of a scalpel blade for the passage of a large caliber cannula. Another limitation of the traditional trocar 39 is that the tissue 25 incisions required for the passage of the traditional trocar 39 usually result in scars. Another limitation of the traditional trocar 39 is to provide a single access-port 3 to the surgical site 26. The Traditional trocars 39 for performing an entry-port 33 in a tissue 25 in a surgery such as robotic surgery, laparoscopic video surgery, video thoracoscopic surgery, cardiac video surgery, arthroscopic video surgery, video urologic surgery, video neurologic surgery, video ophthalmologic surgery, orthopedic video surgery, among other, cause scars. These scars are not desired because, they alter the aesthetics of the body. For example, a professional model, when undergoing gallbladder video surgery, may evolve with unwanted scars from video surgery, which may require restorative plastic surgeries. The possibility of performing a video surgery without a scar is a major evolution in surgery.

Therefore, what is clearly needed is a trocar 34 for providing a plurality of entry-port 33 through a tissue 25 into a surgical site 26, and whose punctures site in the tissue 25 heals by first intention and leaves no visible scars on the tissue 25, and a method for use that solves the problems mentioned above.

SUMMARY OF THE INVENTION

In one embodiment of the invention, a trocar 34 for providing a plurality of entry-port 33 through a tissue 25 into a surgical site 26, containing: a sleeve 9 including a base 10, and a plurality of cannulas 14 connected to said base 10, is provided. Also, in other embodiment said plurality of cannulas 14 is adapted to cause minimal trauma to the tissue 25 in order to prevent scar. Also, in other embodiment, at least, one of said cannulas 14 further comprising a distal piercing tip 2 to puncture the tissue 25. Also, in other embodiment, the invention further comprises a mandrel 1 including a handle 7 and said mandrel 1 including a plurality of piercing tips 2 connected to said handle 7, wherein said mandrel 1 detachably engages the trocar 34 forming a single punch assembly.

In one embodiment of the invention, a trocar 34 for providing a plurality of access-port 3 through tissue 25 into a surgical site 26, containing: a) a sleeve 9 including a base 10, said sleeve 9 including a plurality of cannulas 14 connected to said base 10, b) a mandrel 1 including a handle 7, and said mandrel 1 including a plurality of piercing tip 2 connected to said handle 7, wherein said mandrel 1 detachable engages said sleeve 9 forming a single punch assembly is provided. Also, in other embodiment, said plurality of cannulas 14 has an outer diameter adapted to cause minimal trauma to the tissue 25 in order to prevent scar. Also, in other embodiment, at least one of said plurality of cannulas 14 comprises a dilator 11 to dilating a puncture entry-port 33 in a tissue 25 to prevent scar. Also, in other embodiment, at least one of said plurality of piercing tip 2 comprises a retractable protection system 37. Also, in other embodiment, at least one of said plurality of cannulas 14 comprises a coil 21 which keeps open the access-port 3 of said cannula. Also, in other embodiment, at least one of said plurality of cannulas 14 comprises a fastening system 35 in the tissue 25. Also, in other embodiment, at least one part is made of a transparent material. Also, in other embodiment the invention further includes at least one modular part adapted to connect to other modular part. Also, in other embodiment, the invention further comprises a faucet 12 to control an access of liquids and gases to a surgical site 26. Also, in other embodiment, the invention further comprises a valve 13 to prevent escaping of gas and liquid from the surgical site 26. Also, in other embodiment, the invention further comprises a protector guide 8 to drive and protect the piercing tip 2. Also, in another embodiment, said base 10, is adapted to connect a surgical appliance 36. Also, in other embodiment, at least one of said plurality of cannulas 14 is adapted to connect a surgical appliance 36 in the surgical site 26.

In other aspect of the invention, a method for providing a plurality of entry-port 33 through tissue 25 to the surgical site 26, including: (a) transfixing a trocar 34 including a plurality of cannulas 14 in said tissue 25 to access said surgical site 26, (b) the use of, at least, one of said cannulas 14 as an access-port 3 to said surgical site 26, and (c) removal said plurality of cannulas 14 from said tissue 25, is provided. Also, the method further comprising: (d) detach the mandrel 1 within the sleeve 9, is provided. Also, the method further comprising: (e) connect a surgical appliance 36 to the trocar 34, is provided.

The preferred embodiments according to the invention are shown in FIG. 1-34.

In some embodiments a mandrel 1 may include: a piercing tip 2, a retractable 4, a spring 5, a bezel 6, a handle 7, a female-link 16, a male-link 17, a module 23, a lumen 28, but is not limited to them. In some embodiments a sleeve 9 may include: an access-port 3, a protector guide 8, a base 10, a dilator 11, a faucet 12, a valve 13, a cannula 14, a grooves 15, a male-connector 18, a female-connector 19, a balloon 20, a coil 21, a block 22, a hollow 24, a beater 27, a face 29, a fitting 30, a socket 31, and sharp tip 32, but is not limited to them. Some drawings of some embodiments also include tissue 25, surgical site 26.

BRIEF DESCRIPTION OF THE DRAWINGS

FIG. 9 is a cross-sectional view of other embodiment of the invention, providing two access-port 3 through the tissue 25.

DETAILED DESCRIPTION OF THE PREFERRED EMBODIMENTS

Figure 1:
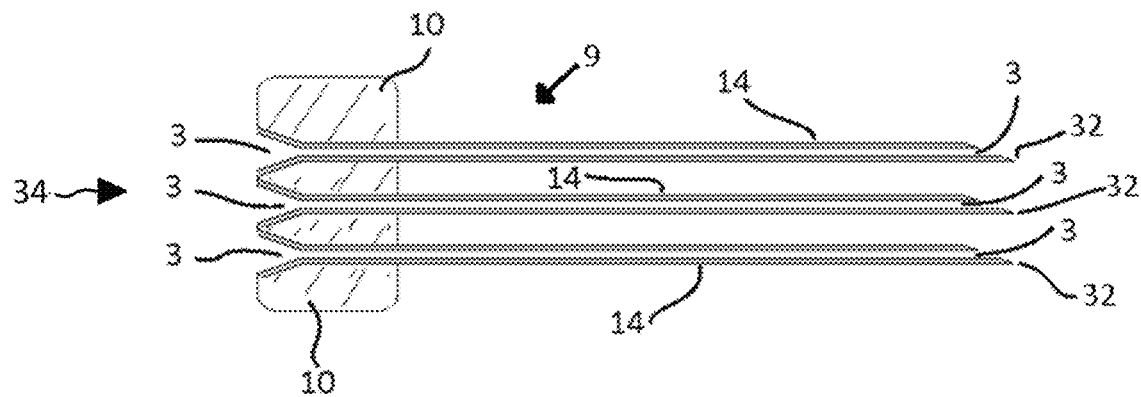
FIG. 1 is a perspective view of one embodiment of the trocar 34 for providing three access-ports 3 through tissue 25 to the surgical site 26.

The inventor provides a trocar 34 for transfixing a plurality of cannulas 14 through a tissue 25 for providing a plurality of access-port 3 through a tissue 25 into the surgical site 26 and whose punctures site in the tissue 25 heals by first intention and leaves no visible scars on the tissue 25, and a method for use that solves the problems mentioned above.

The invention is described in enabling detail in the following examples, which may represent more than one embodiment of the invention, together with the accompanying drawings in which like numerals represent similar components. Additionally, the structures described herein can be embodied as integrated components or as separate components.

FIG. 1. is a sectional view of one embodiment of the invention for providing three access-port 3 through tissue 25 (not seen in the drawing) to the surgical site 26 (not seen in the drawing), including: the sleeve 9 including the base 10, and three cannulas 14 connected to said base 10. In this example, the cannulas 14 are adapted to cause minimal trauma to tissue 25, in order to prevent scar, the cannula 14 has an outer diameter which is adapted to prevent scar formation in the tissue 25. The outer diameter is thin enough to cause minimal trauma to the tissue 25 in order to avoid scarring. In this embodiment, the three cannulas 14 have a distal sharp tip 32 to easily penetrate the tissue 25 and not cause scars. This embodiment does not need the mandrel 1 to puncture the tissue 25, the cannulas 14 are punctured directedly in the tissue 25. This embodiment includes no mandrel 1.

In some embodiments, the trocar 34 comprising the mandrel 1 including the handle 7 and said mandrel 1 including a plurality of the piercing tips 2, connected to said handle 7, wherein said mandrel 1 detachably engages the trocar 34 forming a single punch assembly. In some embodiments, the cannulas 14 have no sharp tip 32.

Figure 2:
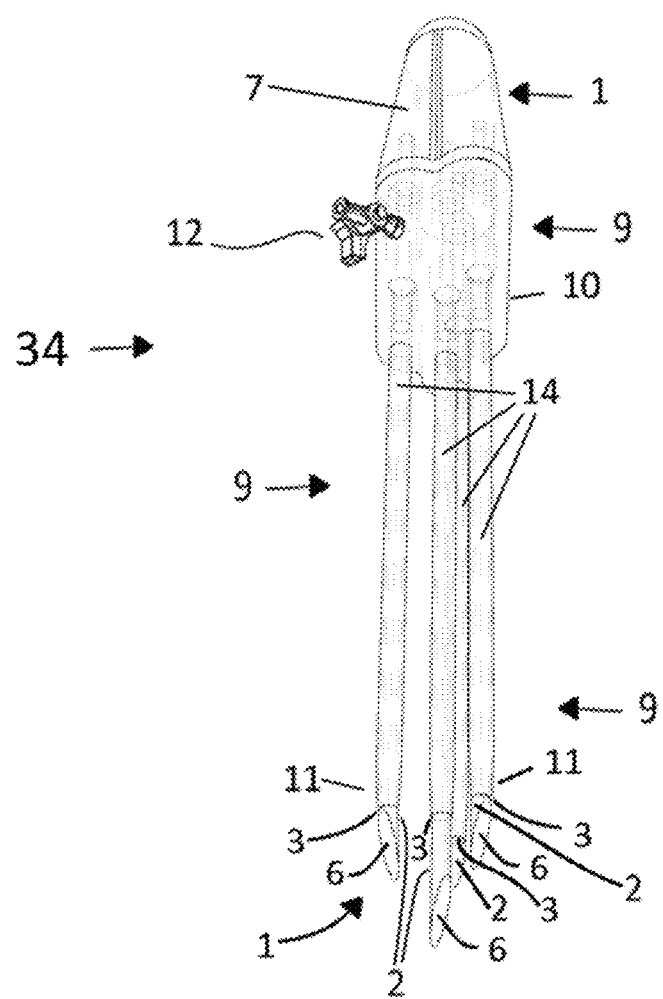
FIG. 2 is a perspective view of one embodiment of the trocar 34 for providing four access-ports 3 through tissue 25 to the surgical site 26.

FIG. 2 is a perspective view of one embodiment of the trocar 34 for providing four access-port 3 through tissue 25 to the surgical site 26, containing: the sleeve 9 including the base 10, and the sleeve 9 including four cannulas 14 connected to the base 10, the mandrel 1 including the handle 7, and the mandrel 1 including four piercing tips 2 connected to the handle 7, wherein the mandrel 1 detachably engage the sleeve 9 forming a single punch assembly.

In this example, the surgeon uses the trocar 34 in a single punch assembly to puncture the tissue 25, the trocar 34 transfixes the tissue 25 at four different entry-ports 33 until each cannula 14 reaches the surgical site 26. In this example, each the piercing tips 2 is solid and includes the bezel 6 shaped tip for facilitating the tissue 25 puncture. Each cannula 14 includes the access-port 3, the four piercing tip 2 are engaged in the four access-ports 3.

Longitudinally sliding the mandrel 1 relative to the sleeve 9 fully detaches the mandrel 1 of the sleeve 9. After the tissue 25 has been transfixed, the surgeon removes the mandrel 1 from the sleeve 9. The sleeve 9 remains in the tissue 25 during surgery so that each cannula 14 provide the access-port 3 through the tissue 25 to the surgical site 26 where surgery will be performed. Each cannula 14 provide the access-port 3. During surgery, the access-port 3 allow insertion into the surgical site 26 of: surgical instruments, parts of surgical instruments, liquids, blood, gases, CO2, but are not limited to them.

In this example, the cannulas 14 are adapted to cause minimal trauma to the tissue 25 in order to prevent scar formation in the tissue 25. The cannula 14 has an outer diameter which is adapted to prevent scar formation in the tissue 25. The outer diameter is thin enough to cause minimal trauma to the tissue 25, in order to avoid scarring at the puncture site. The piercing tips 2 have the bezel 6 sharp to easily penetrate the tissue 25 and not cause scars.

The smaller the external diameter of the cannula 14, the lower the risk of scarring by perforation.

It is widely known that the use of needles to deliver medication including syringes leaves no scar on the tissue 25. The thin needle causes small damage to the tissue 25, that regenerates by first intention without leaving a scar. This example works substantially comparable to a plurality of needles, penetrating different entry-ports 33 of the tissue 25 at the same time. Instead of incising the tissue 25 to insert into the surgical site 26 a conventional single thick trocar 34, which requires a large incision in the tissue 25, the tissue 25 is punctured with this embodiment of the invention which has a plurality of fine the piercing tip 2 each covered by the thin cannulas 14; each the piercing tips 2, of the trocar 34, pierces the tissue 25 and transfixes the tissue 25 until it reaches the surgical site 26. The tissue 25 puncture of the cannulas 14 with the piercing tips 2 engaged function substantially similar to the puncture of an injection needle of a syringe. Also, this embodiment functions substantially similar to the puncture of a venipuncture catheter that does not cause scar.

In this example, the four cannulas 14 comprises, in the distal end, the dilator 11 adapted to dilating a puncture entry-port 33 in the tissue 25. In this example, at the distal end of each cannula 14, there is a conical shaped dilator 11, which dilates the puncture entry-port 33 made by the piercing tips 2 in the tissue 25. This allows for punch into the tissue 25 with the cannula 14 with an outer diameter greater than the puncture entry-port 33 made by the piercing tip 2 without scarring. The trocar 34 assembly performs four punctures on the tissue 25, each puncture including a small diameter, that leave no scar on the tissue 25. After the trocar 34 is removed from the tissue 25, the dilated transfixing orifice retracts, remaining on the tissue 25 only small punctures, which do not cause scarring and do not need to be treated including suture.

In this example, the trocar 34 is made of a transparent material that allows a view of what is in its internal parts during the video-surgery.

In this example, the sleeve 9 has the faucet 12 for controlling the passage of gas and liquid into the surgical site 26 by the access-port 3 of the cannulas 14. The faucet 12 controls the inlet and outlet of gas and liquid from the surgical site 26, the faucet 12 communicates with, at less one, access-port 3 of the four cannulas 14 and allows to inflate gas and liquids in and out of the surgical site 26 (not seen), in accordance with another embodiment of the invention.

In some embodiments, of the invention, the mandrel 1 comprises two piercing tips 2; In some embodiments, of the invention, the mandrel 1 comprises three piercing tips 2; In some embodiments, of the invention, the mandrel 1 comprises four piercing tips 2; In some embodiments, of the invention, the mandrel 1 comprises five piercing tips 2; In some embodiments, of the invention, the mandrel 1 comprises six piercing tips 2; In some embodiments, of the invention, the mandrel 1 comprises seven piercing tips 2; In some embodiments, of the invention, the mandrel 1 comprises eight piercing tips 2; In some embodiments, of the invention, the mandrel 1 comprises nine piercing tips 2; In some embodiments, of the invention, the mandrel 1 comprises ten piercing tips 2, but the number of piercing tips 2 are not limited to them.

In some embodiments, of the invention, the sleeve 9 comprises two cannulas 14; In some embodiments, of the invention, the sleeve 9 comprises three cannulas 14; In some embodiments, of the invention, the sleeve 9 comprises four cannulas 14; In some embodiments, of the invention, the sleeve 9 comprises five cannulas 14; In some embodiments, of the invention, the sleeve 9 comprises six cannulas 14; In some embodiments, of the invention, the sleeve 9 comprises seven cannulas 14; In some embodiments, of the invention, the sleeve 9 comprises eight cannulas 14; In some embodiments, of the invention, the sleeve 9 comprises nine cannulas 14; In some embodiments, of the invention, the sleeve 9 comprises ten cannulas 14, but the number of cannulas 14 in the base 10 are not limited to them.

Figure 3:
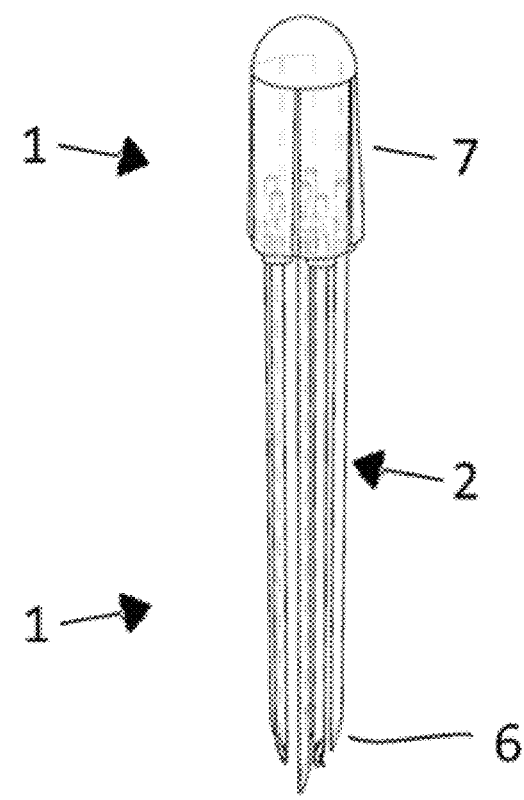
FIG. 3 is a perspective view of another embodiment of the invention, including six cannulas 14 for providing six access-ports 3 through tissue 25 (not seen) to the surgical site 26.
Figure 3:
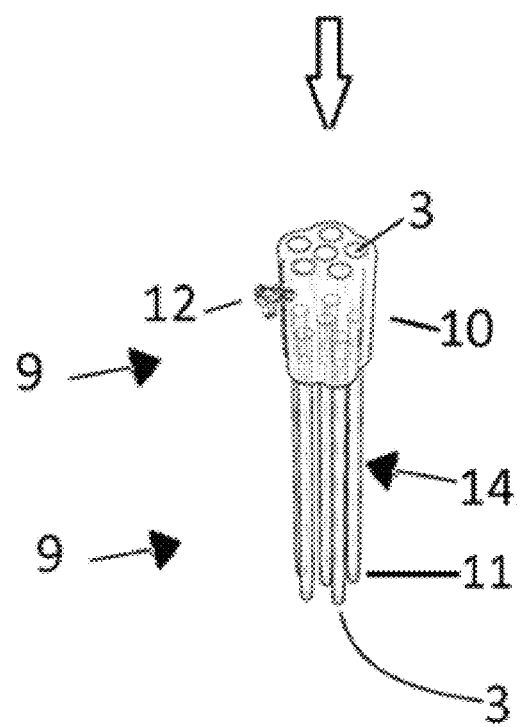

FIG. 3 is a perspective view of another embodiment of the invention, including six cannulas 14 for providing six access-port 3 through tissue 25 (not seen) to the surgical site 26. The arrow shows the direction in which the mandrel 1 slides longitudinally to fit the sleeve 9 perfectly to form a single puncture assembly. In this example, each piercing tips 2 is solid and includes the bezel 6 shaped tip for facilitating the tissue 25 puncture.

In this example, after puncture the tissue 25, the mandrel 1 is completely detachable from the sleeve 9, and the sleeve 9 remains in the tissue 25 during surgery so that each cannula 14 provide the access-port 3 to the surgical site 26 (not seen) to operate the patient. In this example, the faucet 12 controls the passage of gas and liquid through the access-port 3 to the surgical site 26, in accordance with another embodiment of the invention. In some embodiments the trocar 34 is disposable. In some embodiments the trocar 34 is permanent.

Figure 4:
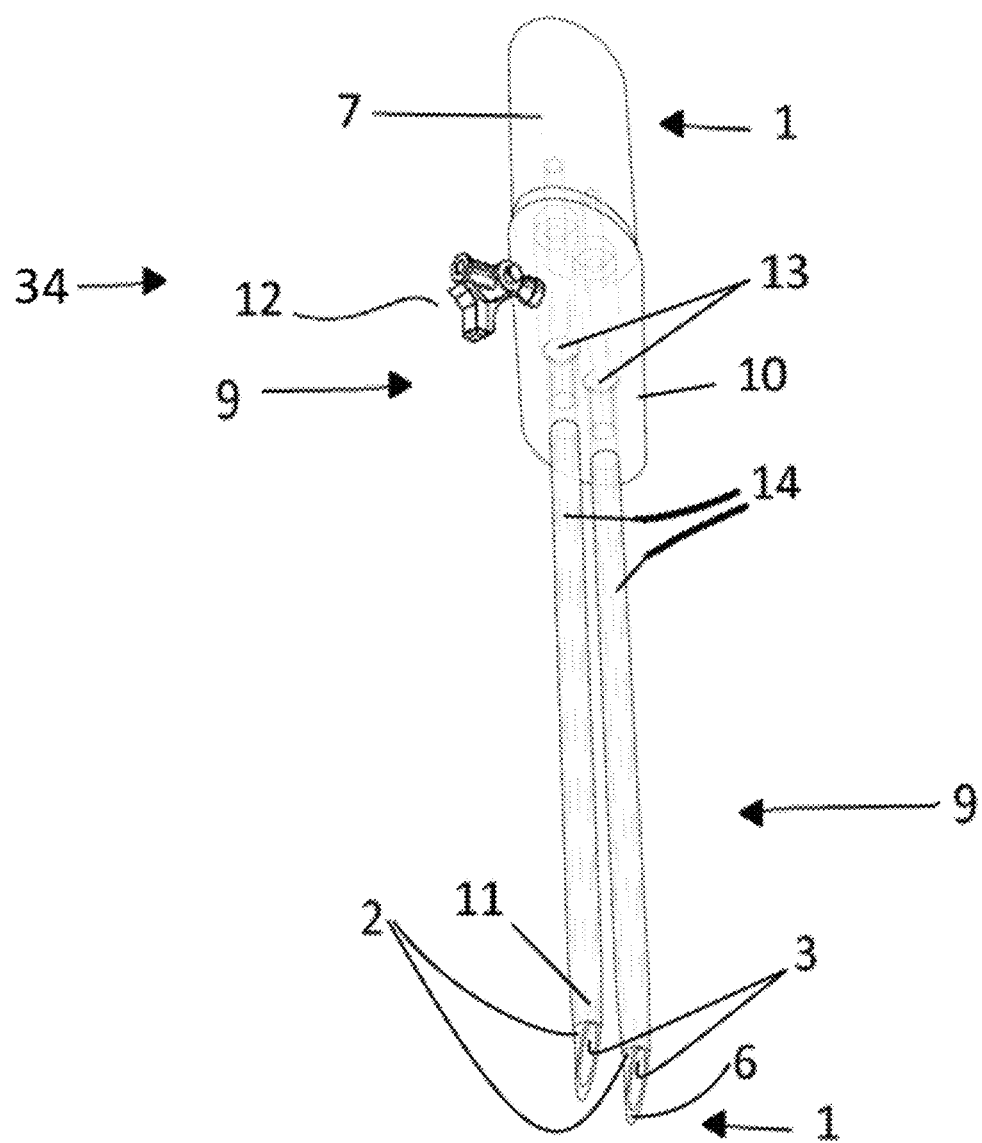
FIG. 4 is a perspective view of another embodiment of the invention for providing two access-ports 3 through tissue 25 to the surgical site 26

FIG. 4 is a perspective view of another embodiment of the invention for providing two access-port 3 through tissue 25 to the surgical site 26, containing: the sleeve 9 including the base 10; said sleeve 9 including two cannulas 14 connected to said base 10; the mandrel 1 including the handle 7; and said mandrel 1 including two piercing tips 2 connected to said handle 7; wherein said mandrel 1 detachably engages said sleeve 9 forming a single punch assembly. The mandrel 1 can be completely detachably from the sleeve 9 by sliding out the mandrel 1 longitudinally relative to the sleeve 9. Each cannula 14 provide the access-port 3 for the surgical site 26. In this example, the valve 13 allows the passage of surgical instruments and parts of surgical instruments, which slide longitudinally within the access-port 3; the valve 13 prevents liquid or gas from returning through the access-port 3 out of the surgical site 26. At the distal end of each cannula 14, there is the wedging shaped dilator 11, which dilates the puncture entry-port 33 made by the piercing tip 2 in the tissue 25. In some embodiments, the dilator 11 have a conical shape, in another embodiments the dilator 11 have a bulged shape, in other embodiments the dilator 11 have a beveled shape, but the dilator 11 shape it is not limited to them.

Figure 5:
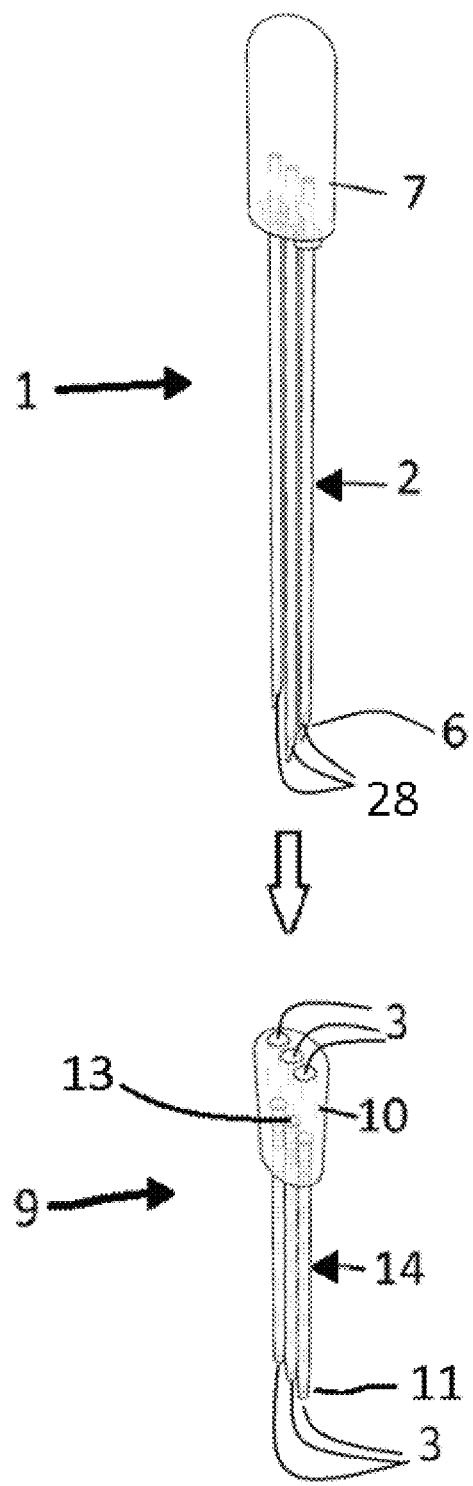
FIG. 5 is a perspective view of another embodiment of the trocar 34, including three cannulas 14 in which the mandrel 1 is not engaged into the sleeve 9.

FIG. 5 is a perspective view of another embodiment of the trocar 34, including three cannulas 14 in which the mandrel 1 is not engaged into the sleeve 9. The arrow shows the direction in which the mandrel 1 slides longitudinally to fit the sleeve 9 perfectly. This example does not have the faucet 12, in accordance with another embodiment of the invention.

Figure 6:
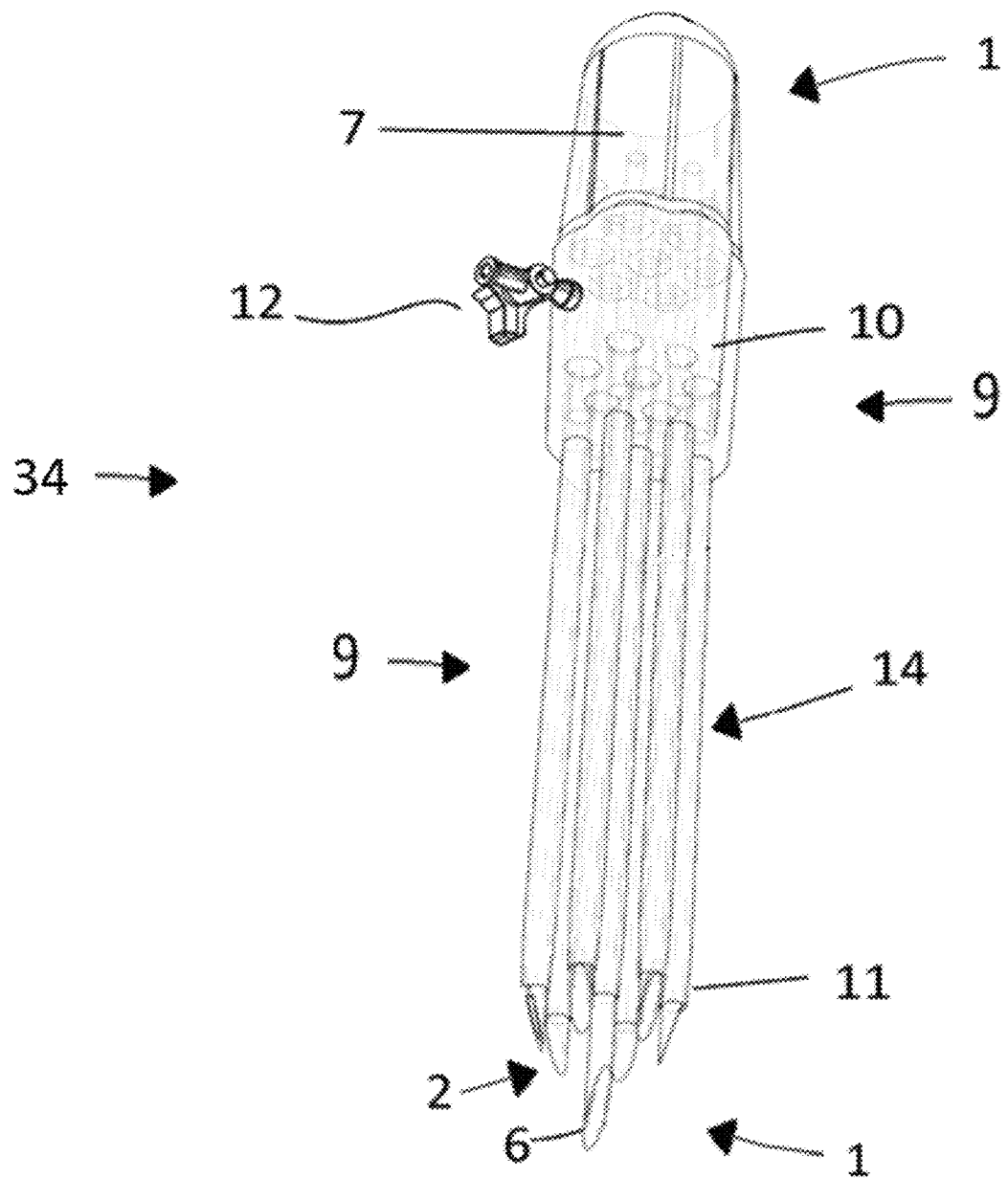
FIG. 6 is a perspective view of other embodiment of the trocar 34 for providing seven access-ports 3 through tissue 25 to the surgical site 26
Figure 7:
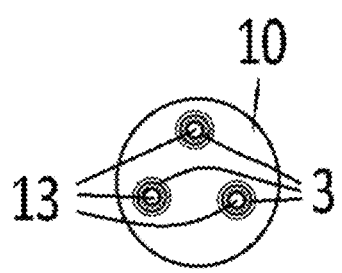
FIG. 7-12 are top views of some embodiments of the invention showing: some base 10, some position of the access-ports 3 in the base 10, and some distribution of the access-port 3 in the base 10.
Figure 8:
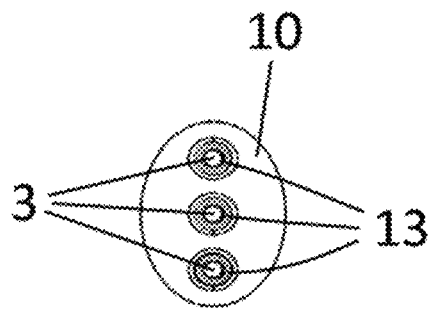
Figure 9:
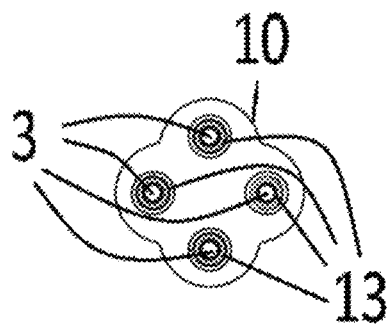
Figure 10:
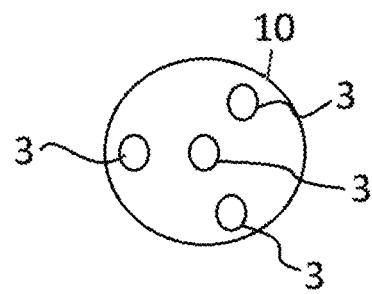
Figure 11:
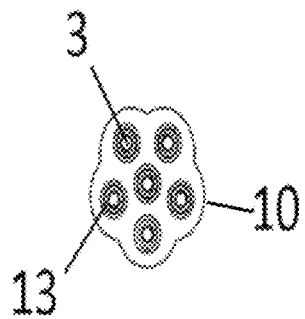
Figure 12:
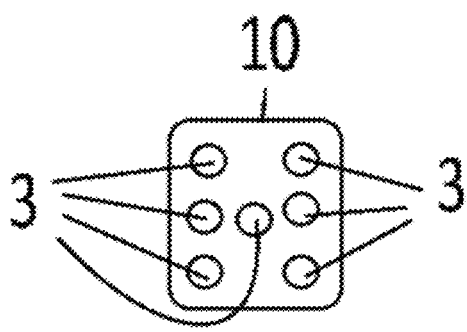

FIG. 6 is a perspective view of other embodiment of the trocar 34 for providing seven access-port 3 through the tissue 25 to the surgical site 26, containing: the sleeve 9 including the base 10, and the sleeve 9 including seven cannulas 14 connected to the base 10, the mandrel 1 including the handle 7; and the mandrel 1 including seven piercing tips 2 connected to the handle 7; wherein the mandrel 1 detachably engages the sleeve 9 forming a single punch assembly. This embodiment includes no valve 13.

FIG. 7-12 are top views of some embodiments of the invention showing: some base 10, some position of the access-port 3 in the base 10, and some distribution of the access-port 3 in the base 10. The cannulas 14 are spaced apart by a distance. The position of the access-port 3 is not limited to them, the number of the access-port 3 is not limited to them. In some embodiments, the transversal shape of the access-port 3 is circular, in some embodiments, the transversal shape of the access-port 3 is elliptical; in some embodiments, the transversal shape of the access-port 3 is square, but the shape of the access-port 3 are not limited to them. The shape of the base 10 is not limited to them. In some embodiments, the trocar 34 includes the valve 13. In other embodiments, the invention does not have the valve 13.

Figure 13:
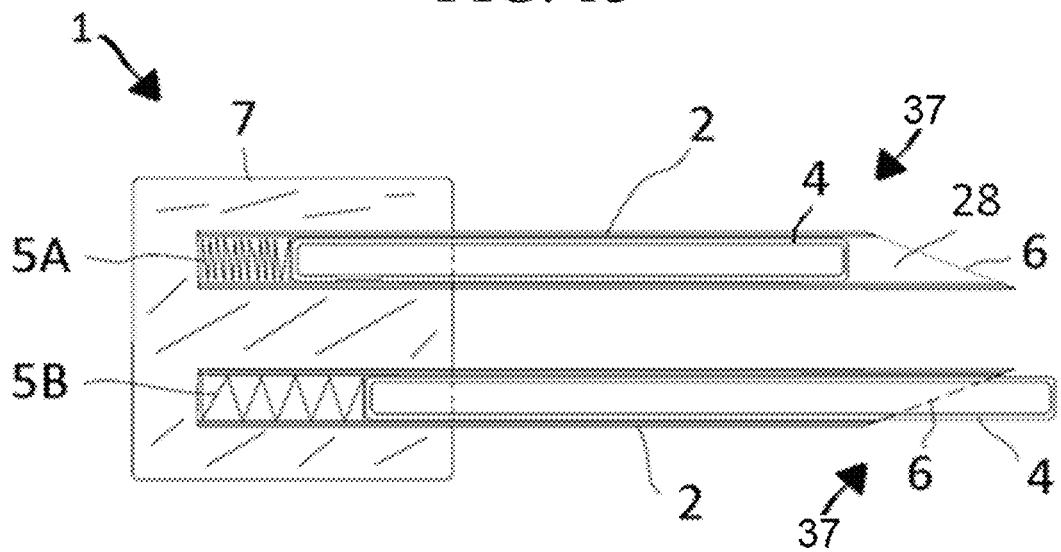
FIG. 13 is a cross-sectional view of other embodiment of the invention, wherein two piercing tips 2 comprise the retractable 4 protection system 37.

FIG. 13 is a cross-sectional view of other embodiment of the invention, wherein two piercing tips 2 comprise the retractable 4 protection system 37. In this example, the mandrel 1 includes two piercing tips 2. The retractable 4 slides longitudinally into the lumen 28 of the piercing tip 2. In this example, the spring 5 is seen in two positions: shrunk position 5A including the retractable 4 fully in the lumen 28 of the piercing tip 2, and in the extended position 5B with the retractable 4 in its distal end out of the lumen 28 of the piercing tip 2. Prior to puncturing the tissue 25, the retractable 4 distal end is out of the lumen 28 of the piercing tip 2 with its distal end externalizing out of the piercing tip 2 and the spring 5 is in an extended position. In the position 5B, the bezel 6 is protected by the retractable 4. When the surgeon pushes the piercing tip 2 to puncture the tissue 25, the retractable 4 is pushed by the tissue 25 and slides longitudinally into the piercing tip 2, and the retractable 4 compresses the spring 5 to position 5A. When the tissue 25 includes been transfixed, the spring 5 returns to the position 5B and, longitudinally, pushes the retractable 4 out of the lumen 28 of the piercing tip 2, in accordance with another embodiment of the invention. In some embodiments, the piercing tip 2 includes the bezel 6 tip to puncture the tissue 25. The bezel 6 angulation is not limited to them. The bezel 6 shape is not limited to them. The bezel 6 shape of edging is not limited to them. In some embodiments, the piercing tip 2 is solid. In some embodiments, the piercing tip 2 includes the lumen 28.

Figure 14:
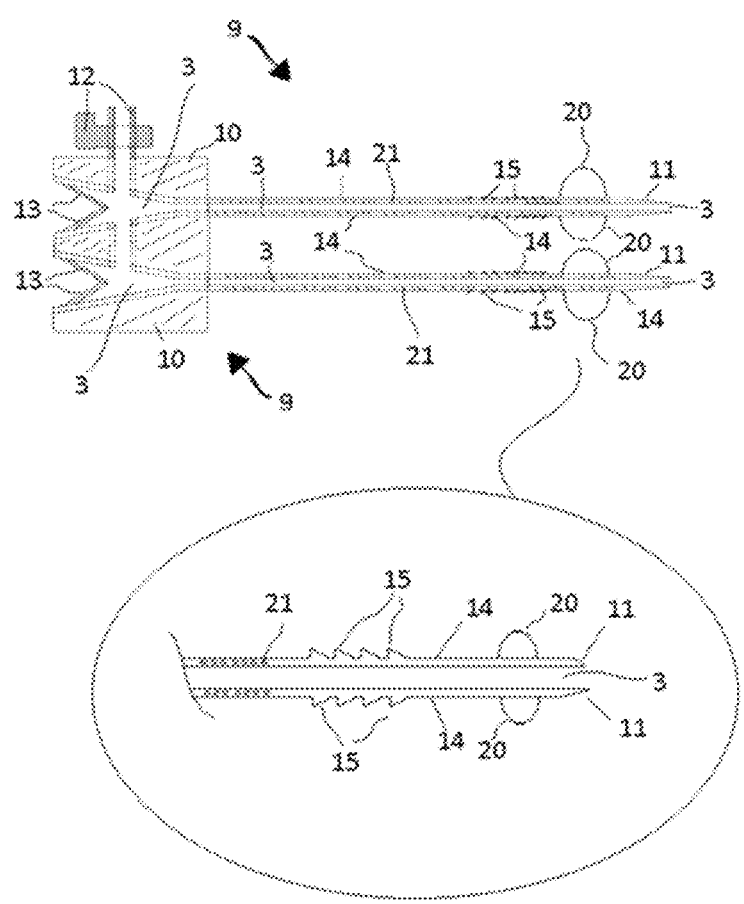
FIG. 14 is a cross-sectional view of another embodiment of the invention, wherein the cannulas 14 comprise the fastening system 35 in the tissue 25, the figure in detail is an ampliation of the distal end of the cannula 14.

FIG. 14 is a cross-sectional view of another embodiment of the invention, wherein the cannulas 14 comprise a fastening system 35 in the tissue 25, the figure in detail is an ampliation of the distal end of the cannula 14.

In this example, the sleeve 9 includes two cannulas 14. They are examples of the fastening system 35: the grooves 15, the balloon 20, but it is not limited to them. The grooves 15 comprise the fastening system 35 and assist in fixing the sleeve 9 in the tissue 25, preventing the cannulas 14, when punched in the tissue 25, to slide longitudinally in the tissue 25 during surgery. The balloon 20 comprises the fastening system 35, the balloon 20 passes deflated through the tissue 25 and it is inflated after the cannula 14 transfixing the tissue 25. In this embodiment, the cannulas 14 comprise the coil 21, which keeps open the access-port 3 of said cannula 14. If the cannula 14 is flexed or folded, the coil 21 maintains pervious the access-port 3. In this example, the dilator 11 is part of the cannulas 14, it is a tapering area thereof, and serves to dilate the puncture entry-port 33 made by the piercing tip 2 (not shown). The faucet 12 may be opened or closed to provide access through the access-port 3 of liquid or gas into the surgical site 26 (not seen). The valve 13 allows the passage of a special surgical instrument, which slides longitudinally in the access-port 3. The valve 13 prevents liquid or gas from returning, from the access-port 3, out of the sleeve 9. At the base 10, the access-port 3 have a cone shape to drive the longitudinal insertion of the surgical instrument into the cannulas 14, in accordance with another embodiment of the invention.

Figure 15:
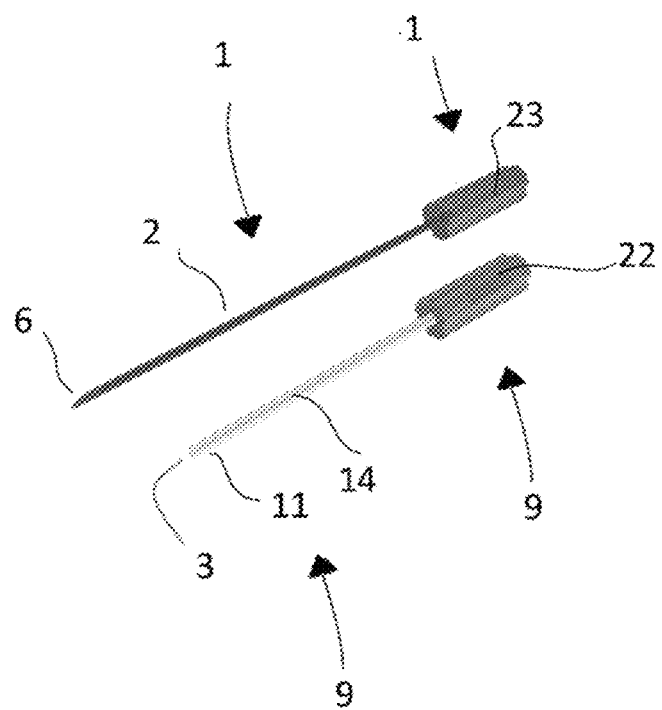
FIG. 15 is a perspective view of another embodiment of the invention, the trocar 34 is modular, including the module 23 and the block 22.

FIG. 15 is a perspective view of another embodiment of the invention, the trocar 34 is modular, including the module 23 and the block 22. In this example, the trocar 34 including the module 23, the module 23 includes six sides. In this example, the module 23 includes a male-female connection 38 to connect to other modules 23, to form the handle 7; the engagement is longitudinally slidable. Also, in this embodiment, the trocar 34 including the block 22 and the block 22 includes six sides. In this example, the block 22 includes male-female connection 38 to connect to other blocks 22 to form the base 10. The engagement is longitudinally slidable. The mandrel 1 is disengaged from the sleeve 9, in accordance with another embodiment of the invention. In some embodiments, the handle 7 will be formed by the connection of, at least, two modules 23, and the base 10 will be formed by the connection of, at least, two blocks 22.

Figure 16:
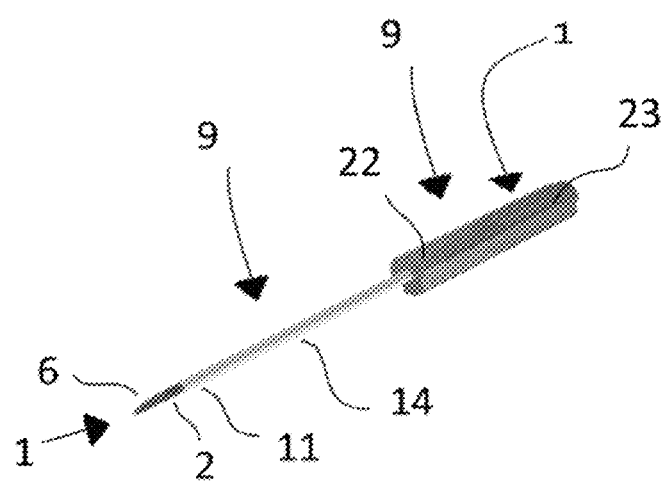
FIG. 16 is a perspective view of another embodiment of the invention, the trocar 34 is modular, the mandrel 1 is engaged in the sleeve 9.

FIG. 16 is a perspective view of another embodiment of the invention, the trocar 34 is modular, the mandrel 1 is engaged in the sleeve 9. In this example, the trocar 34 is ready to connect to other trocars 34 assembly by a male-female connection 38; the engagement is longitudinally slidable by the six sides. In this example, the trocar 34 is modular including the module 23 and the block 22, the mandrel 1 is perfectly engaged in the sleeve 9, forming a single punch assembly. The module 23 connects perfectly to the block 22. The module 23 is made to connect other modules 23. The block 22 is made to connect other blocks 22, in accordance with another embodiment of the invention.

Figure 17:
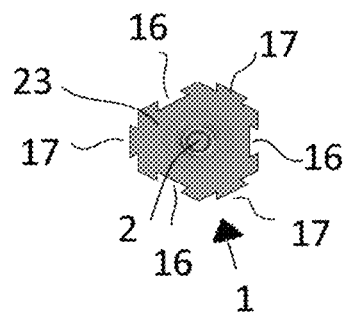
FIG. 17 is a top view of other embodiment of the invention, the module 23, in this example, the module 23 includes six sides: three sides including the female-link 16, and the other three sides including the male-connector 17.

FIG. 17 is a top view of other embodiment of the module 23, in this example, the module 23 includes six sides: three sides including the female-link 16, and the other three sides including the male-connector 17. Each male-link 17 is shaped to engage the female-link 16 of another module 23. The engagement is longitudinally slidable, the female-link 16 is constructed to fit longitudinally slidable in the male-link 17 of another module 23, the male-link 17 is constructed to fit longitudinally slidable in the female-link 16 of another module 23, in accordance with another embodiment of the invention.

Figure 18:
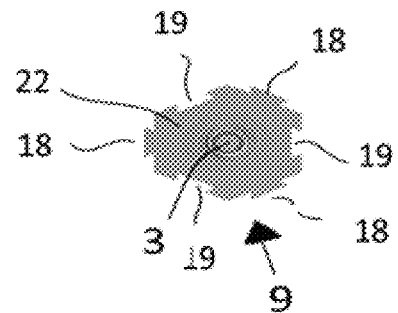
FIG. 18 is a top view of other embodiment of the invention, of the block 22, in this example, the block 22 includes six sides: three sides including the female-connector 19, three sides including the male-connector 18

FIG. 18 is a top view of other embodiment of the block 22, in this example, the block 22 includes six sides: three sides including the female-connector 19, three sides including male-connector 18. Each male-connector 18 is shaped to engage the female-connector 19 of another block 22. The engagement is longitudinally slidable, the male-connector 18 is constructed to fit, longitudinally slidable, in the female-connector 19 of another block 22, the female-connector 19 is constructed to fit, longitudinally slidable, in the male-connector 18 of another modular block 22, in accordance with another embodiment of the invention.

Figure 19:
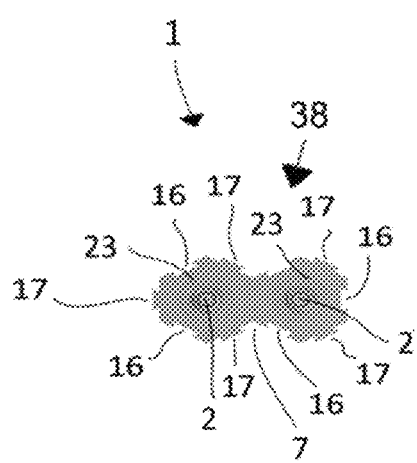
FIG. 19 is a top view of another embodiment of the invention comprising four blocks 22.

FIG. 19 is a top view of other embodiment of the invention comprising two connected modules 23. In this example, the handle 7 is modular and formed by the joint of two or more module 23, engaged in one another in a longitudinal sliding manner by male-female connection 38. The female-link 16 is slidably engaged in the male-connector 17 of another module 23, forming the handle 7, including two modules 23. In some embodiments, the handle 7 is formed by connecting of a plurality of modules 23, but the number of modules 23 is not limited to them. The forms of engagement of the modules 23 are not limited to them, in accordance with another embodiment of the invention.

Figure 20:
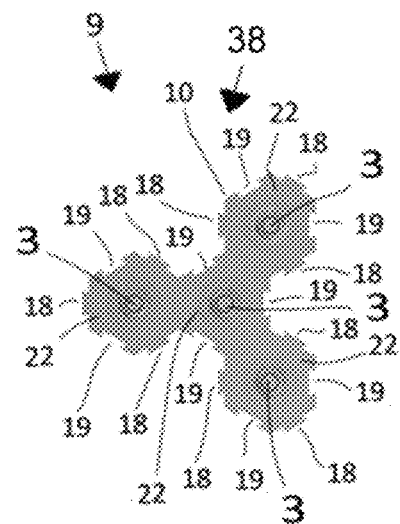
FIG. 20 is a top view of another embodiment of the invention, comprising four connected blocks 22.

FIG. 20 is a top view of another embodiment of the invention, comprising four connected blocks 22. In this embodiment, the base 10 is modular and formed by the connection of four blocks 22 connected to a longitudinal sliding manner.

Figure 21:
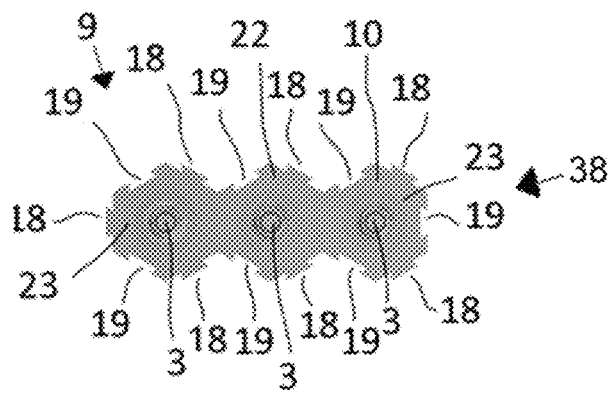
FIG. 21 is a top view of another embodiment of the invention, comprising three blocks 22.

FIG. 21 is a top view of another embodiment of the invention, comprising three blocks 22. In this example, the base 10 is modular and formed by the connection of three blocks 22 connected in a longitudinal sliding manner. In this embodiment, the sleeve 9 is made by the connection of three blocks 22.

Figure 22:
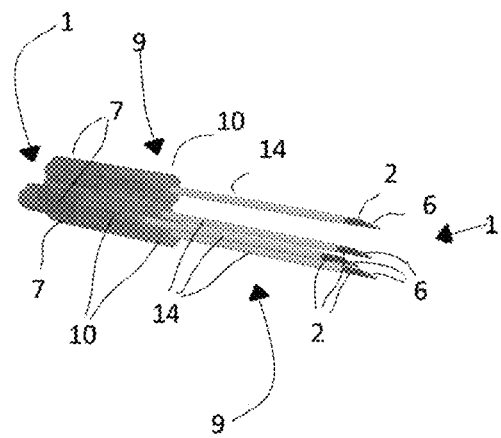
FIG. 22 is a perspective view of other embodiment of the invention, the trocar 34 is modular, comprising four connected modules 23 and four connected blocks 22.

FIG. 22 is a perspective view of other embodiment of the invention, the trocar 34 is modular, including male-female connections 38, comprising four connected modules 23 and four connected blocks 22. The mandrel 1 is perfectly engaged in the sleeve 9. The module 23 is perfectly engaged in the block 22. In this example, the mandrel 1 is formed by four connected modules 23, sliding longitudinally, the sleeve 9 is formed by four blocks 22 connected longitudinally slidably engaged. The mandrel 1, detachably engages, the sleeve 9, forming a single punch assembly.

Figure 23:
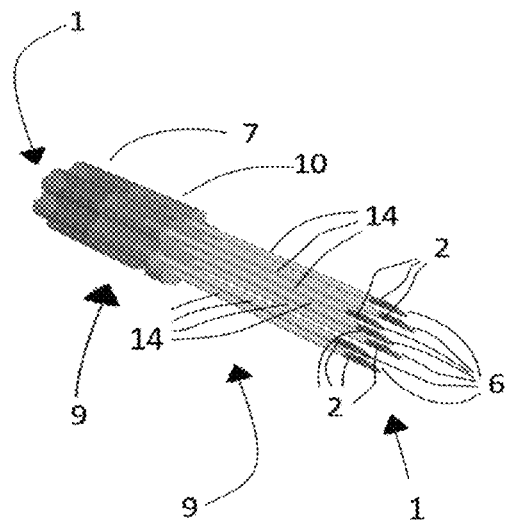
FIG. 23 is a perspective view of another embodiment of the invention. The trocar 34 is modular comprising seven connected modules 23 and seven connected blocks 22.

FIG. 23 is a perspective view of another embodiment of the invention. The trocar 34 is modular comprising seven connected modules 23 and seven connected blocks 22. The mandrel 1 is perfectly engaged in the sleeve 9. In this example, the handle 7 is formed by seven modules 23 slidable engaged longitudinally, the base 10 is formed by seven blocks 22, which are longitudinally slidably engaged. The mandrel 1, detachably engages the sleeve 9 forming a single punch assembly, in accordance with another embodiment of the invention, according to another embodiment of the invention.

Figure 24:
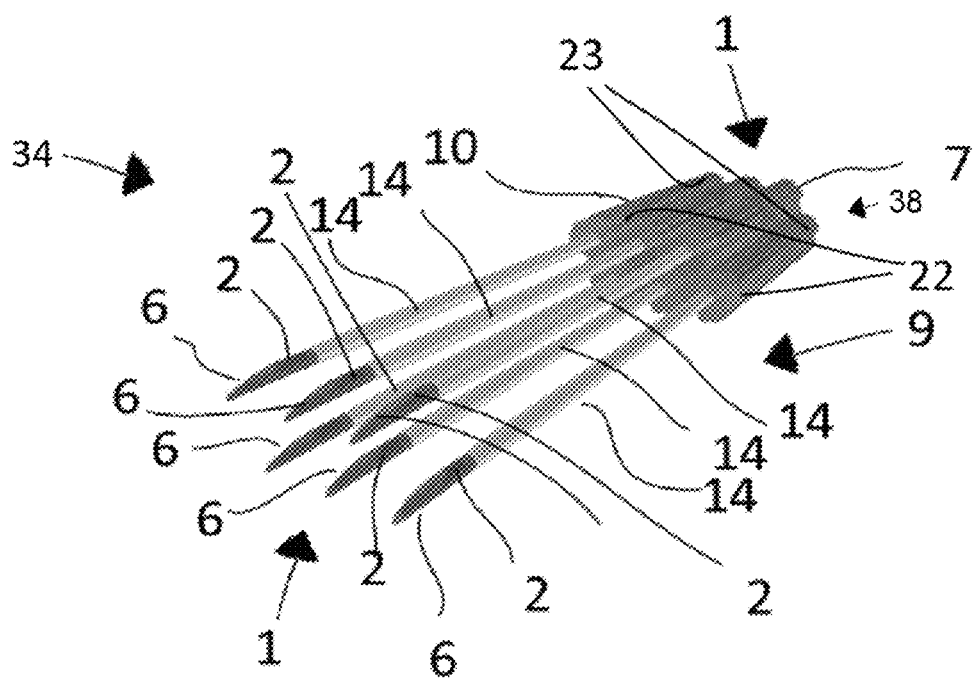
FIG. 24 is a perspective view of another embodiment of the invention, the six modules 23 are connected in a suitable way to puncture the intercostal space, it is made to accompanying the shape of the ribs in the chest.

FIG. 24 is a perspective view of another embodiment of the invention, the six modules 23 are connected in a suitable way to puncture the intercostal space, it is made to accompanying the shape of the ribs in the chest. The trocar 34 is modular comprising six connected modules 23 and six connected blocks 22. The mandrel 1 is perfectly engaged in the sleeve 9, the module 23 engages perfectly into the block 22. In this example, the mandrel 1 is formed by six modules 23 connected modularly sliding longitudinally, the sleeve 9 is formed by six blocks 22 connected longitudinally slidably engaged. The mandrel 1 detachably engages the sleeve 9 forming a single punch assembly, in accordance with another embodiment of the invention.

Figure 25:
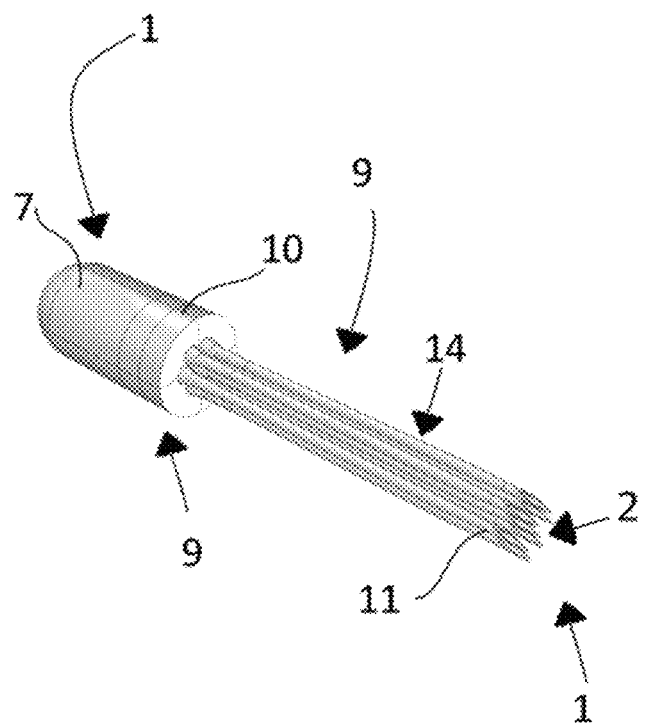
FIG. 25 is a perspective view of another embodiment of the invention in a modular configuration for providing seven access-ports 3 through the tissue 25 (not seen in the drawing) to the surgical site 26 (not seen in the drawing).

FIG. 25 is a perspective view of another embodiment of the invention including male-female connection 38 for providing seven access-port 3 through tissue 25 (not seen in the drawing) to the surgical site 26 (not seen in the drawing). The mandrel 1 is modular and perfectly engaged into the modular sleeve 9 forming a single punch assembly. In this example, the mandrel 1 is modular comprising of the handle 7 connected to seven piercing tips 2, and the sleeve 9 is modular comprising the base 10 connected to seven cannulas 14. In this example, the mandrel 1 can be completely detachably from the sleeve 9, by sliding the mandrel 1 longitudinally relative to the sleeve 9. In this example, the handle 7 is modular and includes seven female-link 16 (not seen in the drawing) connected in seven modules 23 (not seen in the drawing). In this example, each module 23 includes the piercing tip 2. The sleeve 9 is modular and includes the base 10 including seven female-connector 19 (not seen in the drawing), seven blocks 22 (not seen in the drawing) embedded in the female-connector 19. Each block 22 includes the cannula 14, according to another embodiment of the invention.

Figure 26:
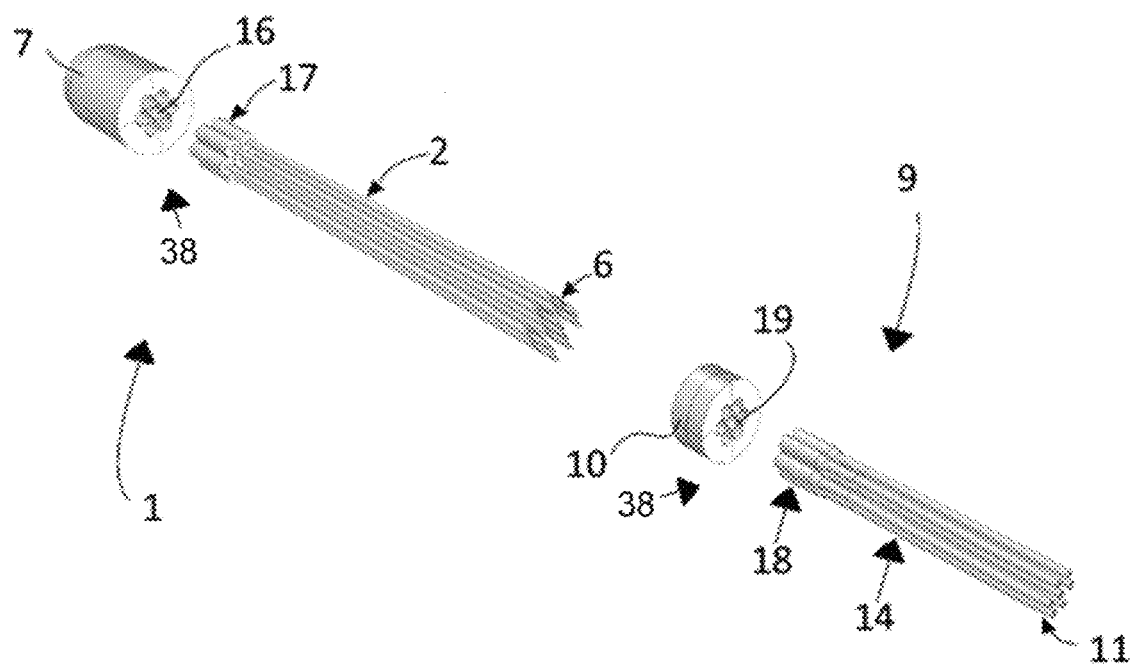
FIG. 26 is a perspective view of another embodiment of the invention, the male-female-connections 38 are disconnected.

FIG. 26 is a perspective view of another embodiment of the invention, the male-female connection 38 are disconnected. This embodiment, containing: the handle 7 including seven female-links 16 and the base 10 including seven female-connectors 19. Each male-link 17 connects the female-link 16 in longitudinal sliding movement. In this example, the surgeon chooses the number of piercing tips 2 that will be engaged in the handle 7. The sleeve 9 includes the base 10 including seven female-connectors 19, each cannula 14 includes the male-connector 18 that connects the female-connector 19. In this embodiment, the surgeon chooses the number of cannulas 14 to fit into the base 10, in accordance with another embodiment of the invention. In some embodiments, the shape, the size, and the types of the modular parts are different.

Figure 27:
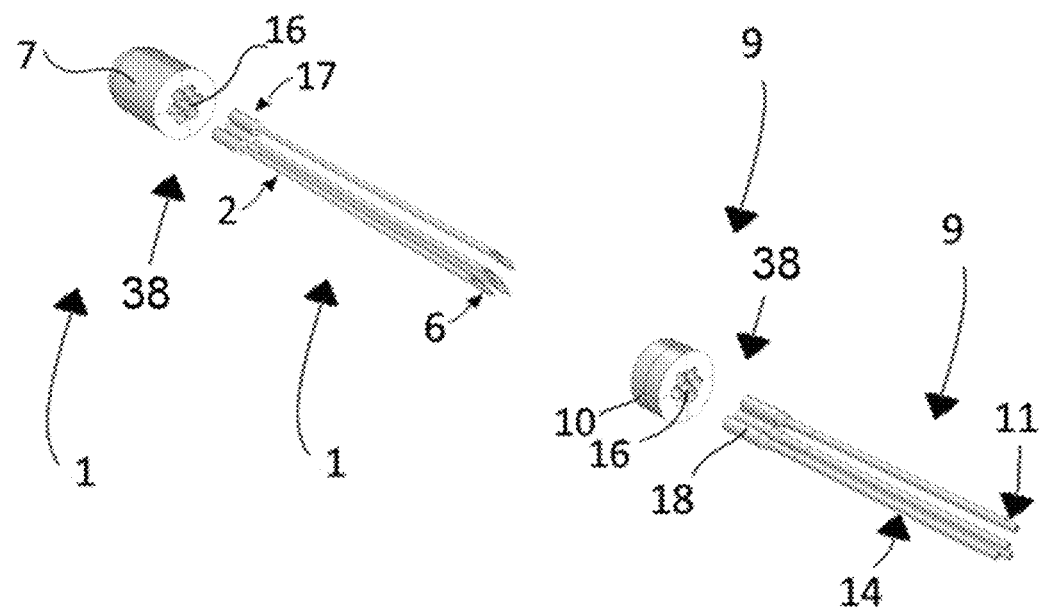
FIG. 27 is a perspective view of another embodiment of the invention, comprising: seven female-links 16 to connect four male-links 17 and seven female-connectors 19 to connect four male-connectors 18 of the male-female connection 38.

FIG. 27 is a perspective view of another embodiment of the invention, comprising: seven female-links 16 to connect four male-links 17 and seven female-connectors 19 to connect four male-connectors 18. In this example, the surgeon chooses in which of the seven female-links 16 connect the four male-links 17 and in which of the seven female-connectors 19 connects the four male-connectors 18. In this example, the modular parts are disconnected. In this embodiment, the mandrel 1 includes the handle 7 including seven female-links 16, four male-links 17 of the piercing tips 2 are aligned for connect in the female-link 16 in a longitudinal sliding movement. The sleeve 9 includes the base 10, including seven female-connectors 19, four male-connectors 18 of the cannulas 14 are aligned to fit in the female-connector 19 in a longitudinal sliding movement, in accordance with another embodiment of the invention.

Figure 28:
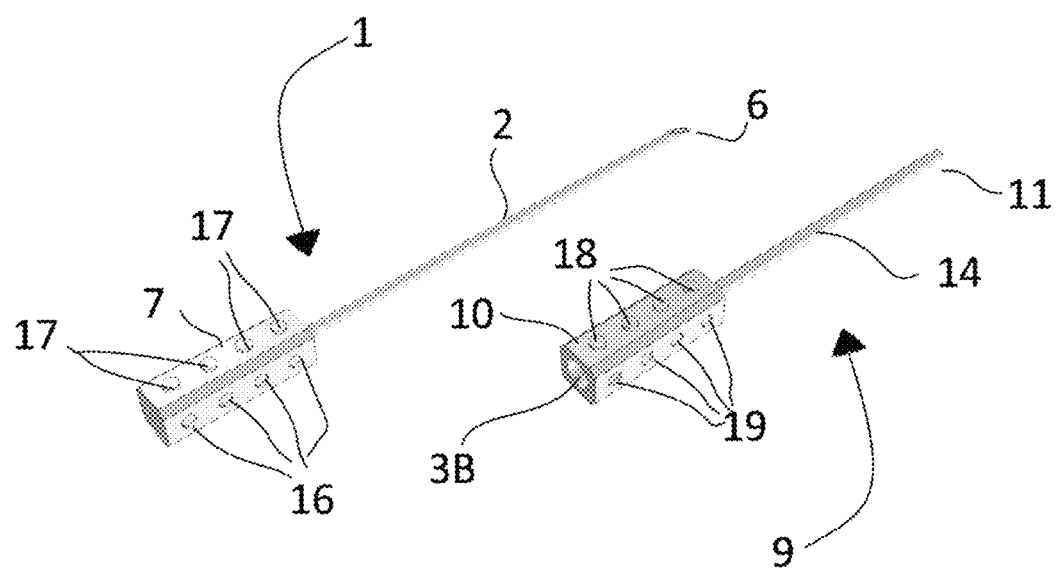
FIG. 28 is a perspective view of another embodiment of the invention in a modular configuration including male-female connections 38.

FIG. 28 is a perspective view of another embodiment of the invention including male-female connection 38. The handle 7 includes four sides, being two sides including the male-link 17 and two sides including female-link 16. The base 10 also has four sides, being two sides including male-connector 18 and two sides including female-connector 19. In this example, the modular parts connect substantially similar to the "Lego Toy" male-to-female connectors.

Figure 29:
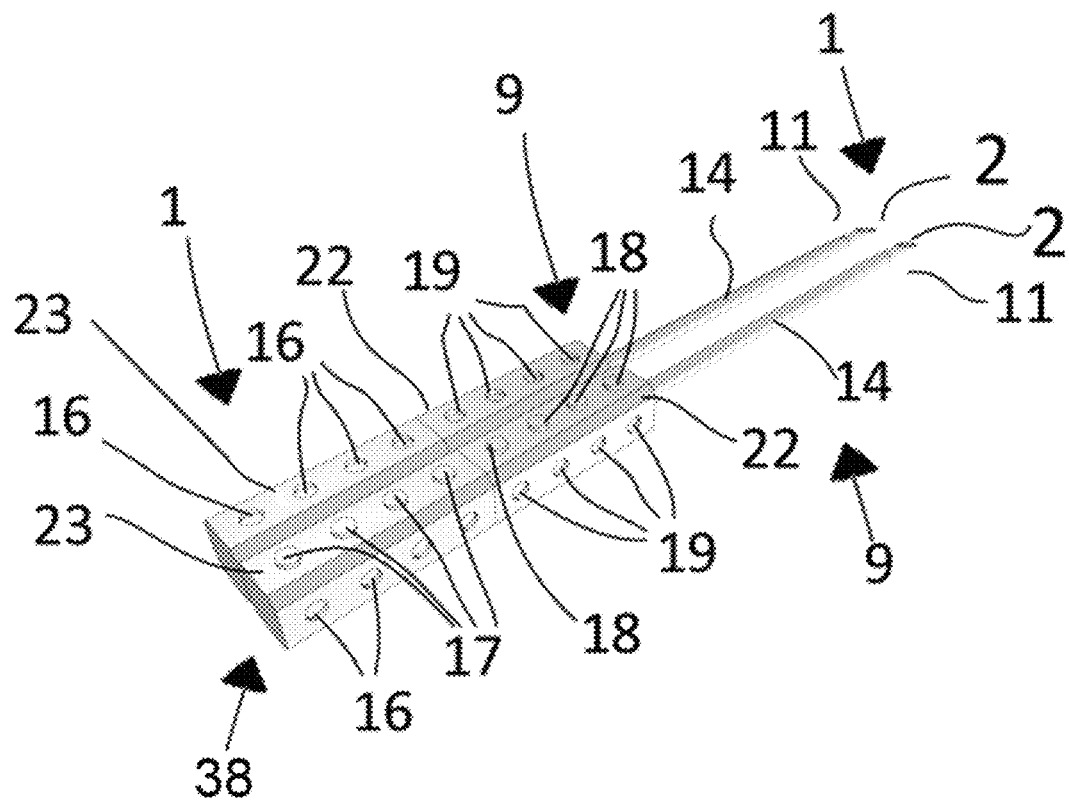
FIG. 29 is a perspective view of another embodiment of the invention, in a modular configuration including male-female connections 38 with four connection sides.

FIG. 29 is a perspective view of another embodiment of the invention, in a modular configuration including four connection sides. In this example, the mandrel 1 includes the handle 7 modular formed by the connection of two modules 23 and the sleeve 9 includes the modular base 10 formed by the connecting of two blocks 22. In this example, the mandrel 1 is perfectly engaged in the sleeve 9, the mandrel 1 includes the handle 7 modular formed by the connection of two modules 23, one module 23 is connected side by side to another module 23, four male-links 17 of the module 23 are connected to four female-link 16 of the other module 23. Each module 23 includes four connection sides, each side includes four connectors being two sides including four male-links 17 and two sides including four female-links 16. Each module 23 includes the piercing tip 2, in accordance with another embodiment of the invention.

In this example, the sleeve 9 includes the modular base 10 formed by the connecting of two blocks 22, which are connected side by side to another block 22. Each block 22 includes four connection sides. In this example, four male-connectors 18 of one block 22 are connected to four female-connectors 19 of the other block 22. In a cross-section view each block 22 includes four sides, each side including four connectors, two sides being including four male-connectors 18 and two sides being including four female-connectors 19. Each block 22 includes the cannula 14. The mandrel 1, detachably engages the sleeve 9 forming a single punch assembly, according to another embodiment of the invention.

Figure 30:
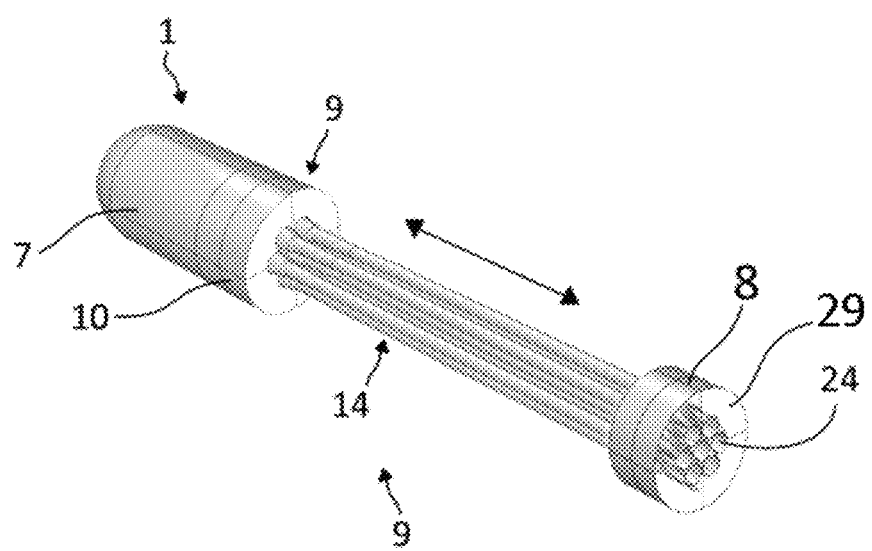
FIG. 30 is a perspective view of another embodiment of the invention, including the protector guide 8.

FIG. 30 is a perspective view of another embodiment of the invention, including the protector guide 8. The protector guide 8 is on the cannula 14. The protector guide 8 is movable over the cannula 14 and can be moved from the base 10 to the distal end of the cannula 14. When positioned in the distal position of the cannula 14, it protects the dilator 11 and protects the bezel 6 of the piercing tip 2. In this example, there is the beater 27 (not seen) at the distal end of the cannula 14, which prevents the protector guide 8 of coming out of the cannulas 14. The protector guide 8 includes a protective function, so the bezel 6 does not injure something inadvertently and includes the hollows 24 for direct correctly the penetration of the cannulas 14 into the tissue 25. The two-headed arrow indicates the movement of the hollow 24 on the cannula 14, according to another embodiment of the invention.

FIG. 31, FIG. 32, FIG. 9, and FIG. 34 are cross-sectional views of some embodiments of the invention, including the method of providing a plurality of access-port 3 through tissue 25 to the surgical site 26. The method of providing a plurality of access-port 3 through tissue 25 to the surgical site 26, including: (a) transfixing a trocar 34 comprising a plurality of cannulas 14 in said tissue 25 to access said surgical site 26, (b) using, at least, one access-port 3 to access said surgical site 26; and (c) removing the trocar 34 of said tissue 25, is provided. The methods further include (d) detach the mandrel 1 within the sleeve 9; (e) connecting a surgical appliance 36 to the trocar 34 is provided. The acts or operations of the method or process can be performed in any suitable sequence and are not necessarily limited to any particular disclosed sequence. FIG. 31, FIG. 32, FIG. 9, and FIG. 34 are described in more detail below, according to some embodiments of the invention.

Figure 31:
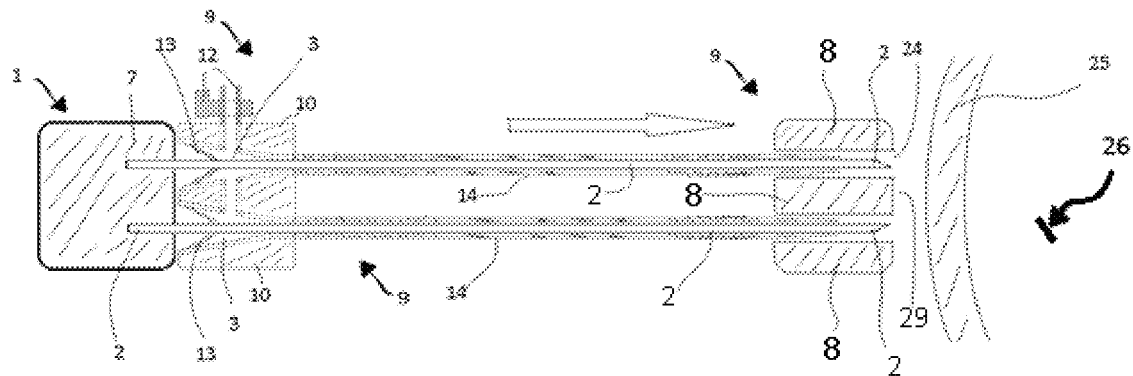
FIG. 31 is a cross-sectional view of other embodiment of the invention, the protector guide 8 is positioned at the distal end of the cannulas 14.

FIG. 31 is a cross-sectional view of other embodiment of the invention, the protector guide 8 is positioned at the distal end of the cannulas 14. The bezel 6 and the dilator 11 are protected inside the hollow 24. The beater 27 prevents the protector guide 8 from coming out of the cannulas 14. The mandrel 1 and the sleeve 9 form a single punch assembly to puncture the tissue 25 for providing a plurality of access-port 3 through tissue 25 to the surgical site 26, according to another embodiment of the invention.

In this example, the protector guide 8 includes the hollow 24 through which the cannulas 14 pass. In this example, the protector guide 8 has two functions: driving the piercing tips 2 during the tissue 25 puncture and protecting the bezel 6 so as not to, inadvertently, injure something. Transfixing the trocar 34 comprising two cannulas 14 in said tissue 25 to access said surgical site 26. In this example, for the trocar 34 puncture of the tissue 25, the surgeon abuts the face 29 of the protector guide 8 to the tissue 25 and pushes the trocar 34 against the tissue 25. The hollows 24 of the protector guide 8 drive the piercing tips 2 that perforate the tissue 25 in a driveway, according to another embodiment of the invention.

Figure 32:
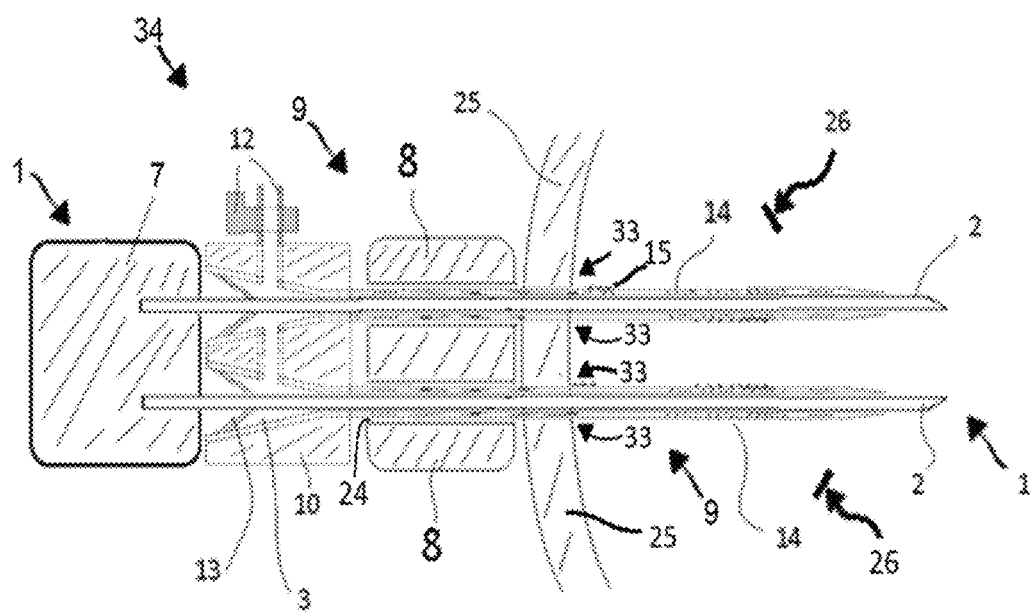
FIG. 32 is a cross-sectional view of other embodiment of the invention.

FIG. 32 is a cross-sectional view of other embodiment of the invention, including the method of transfixing a trocar 34 comprising two cannulas 14 in the tissue 25 to access the surgical site 26. In this example, the mandrel 1 and the sleeve 9 form a single punch assembly which has been punctured in the tissue 25. In this example, the cannulas 14 passed through the protector guide 8 through the hollow 24, traversed the tissue 25 and reached the surgical site 26. In this example, the dilator 11 dilated the entry-port 33 made by the piercing tip 2, allowing the passage of the cannulas 14. The hollow 24 is positioned in the proximal end of the cannula 14 near the base 10. The mandrel 1 has not yet been detachable from the sleeve 9, the piercing tip 2 is inside the cannulas 14 and the bezel 6 is inside the surgical site 26. In this example, to use the access-port 3 the surgeon detaches the mandrel 1 within the sleeve 9 by longitudinal traction.

Figure 33:
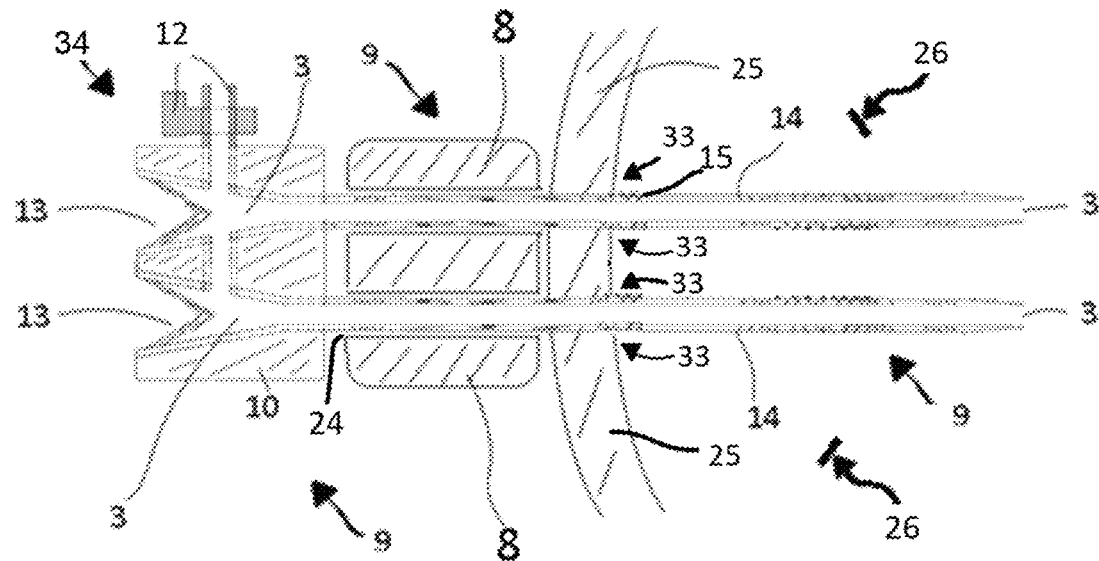

FIG. 33 is a cross-sectional view of other embodiment of the invention, providing two access-port 3 through the tissue 25. The cannulas 14 are spaced apart by a distance. The mandrel 1 (not seen in the drawing) has been detachable from the sleeve 9 by longitudinal traction. In this example, the sleeve 9 is positioned in the tissue 25 and is now an access-port 3 through tissue 25 of the video instrument to the surgical site 26. The cannulas 14 of the sleeve 9 are traversing the tissue 25. The valves 13 prevent gas or liquid from flowing out of the surgical site 26. The faucet 12 allows the inflation of gas or liquid into the surgical site 26. The fastening system 35 comprising grooves 15 secure the cannulas 14 in the tissue 25 and prevent the cannula 14 from sliding on the tissue 25. In this example, the surgeon using, at least, one access-port 3 to access said surgical site 26, the access-port 3 allow insertion into the surgical site 26 of: surgical instruments, parts of surgical instruments, liquids, blood, gases, CO2, but are not limited to them. Removing the plurality of cannulas 14 from the tissue 25, after the surgery, the trocar 34 is removed from the tissue 25 by longitudinal traction, according to another embodiment of the invention.

Figure 34:
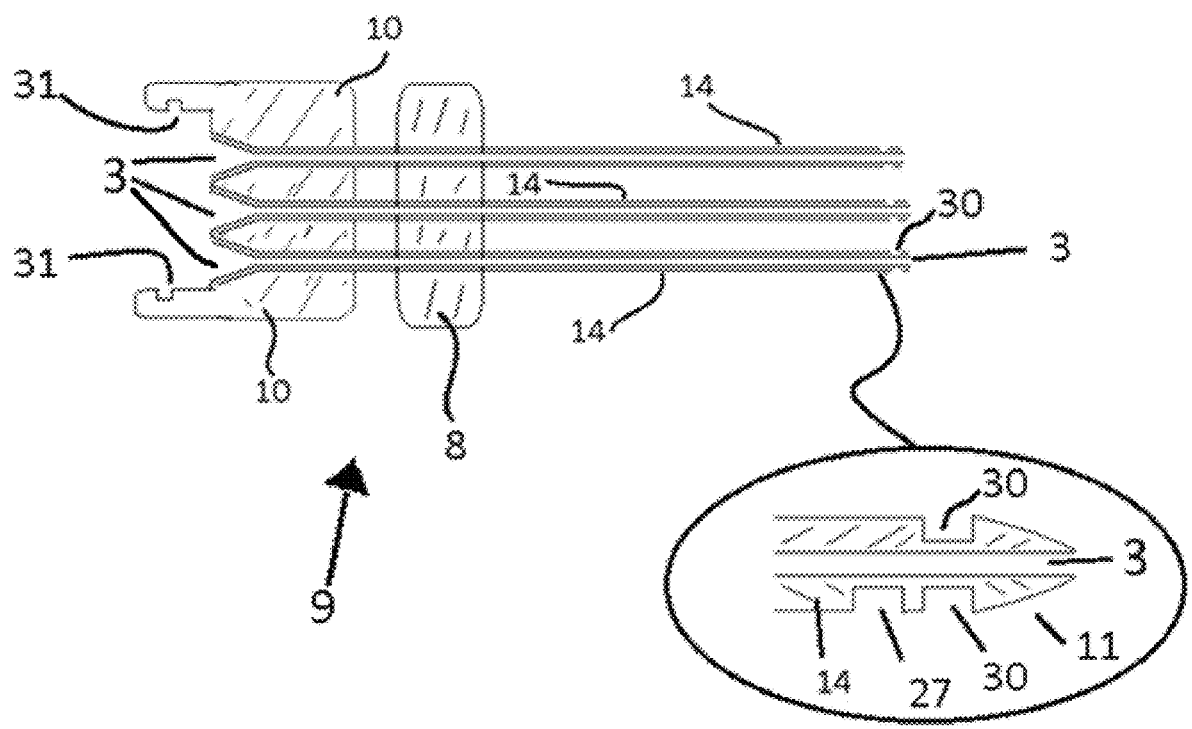
FIG. 34 is a cross-sectional view of another embodiment of the invention that is adapted to connect to at least one surgical appliance 36. The detail of the drawing shows the distal end of the cannula 14, according to one embodiment of the invention.

FIG. 34 is a cross-sectional view of another embodiment of the invention that is adapted to connect to at least one surgical appliance 36. In the detail is a drawing showing the distal end of the cannula 14, according to one embodiment of the invention. In this example, the trocar 34 provides three access-port 3 through the tissue 25 into the surgical site 26. The trocar 34, including: the base 10; and a plurality cannula 14 connected to the base 10. The three cannulas 14 are adapted to cause minimal trauma to the tissue 25 in order to prevent scar, the cannulas 14 are thin enough to cause minimal trauma to the tissue 25. Also, the three cannulas 14 further including the distal sharp tip 32 to puncture the tissue 25 avoiding scaring the tissue 25. In this example the base 10 including the socket 31. The cannulas 14 including the beater 27 and the fitting 30, according to another embodiment of the invention.

Connecting a surgical appliance 36 to the trocar 34, in this example, the base 10 is adapted to connect a surgical appliance 36 in the base 10. In this example, at least one surgical appliance 36 may be connected to socket 31, but it is not limited to them. In this embodiment, there are some surgical appliances 36 that may be connected to the base 10: a hose, a suction appliance, a cannula, a video camera, guide, introduction guide, a surgical instrument, an electronic appliance, a surgical robot, an adapter, a video camera, a cable, a pneumatic appliance, but it is not limited to them. In some embodiments, a surgical appliance 36 is connected the trocar 34 in a detachably engages way. In some embodiments, the connection of the surgical appliance 36 to the base 10 is in a sealant way. In some embodiments, the connection of the surgical appliance 36 to the base 10 is in a non-sealant way. In some embodiments, the connection of the surgical appliance 36 to the base 10 is in a removable way. In some embodiments, the connection of the surgical appliance 36 to the base 10 is in a non-removable way, but it is not limited to them. In some embodiments, the connection of the surgical appliance 36 to the base 10 is made by friction. In some embodiments, the connection of the surgical appliance 36 to the base 10 is made by electrical connection. In some embodiments, the connection of the surgical appliance 36 to the base 10 is made by mechanical connection, but the type of connection is not limited to them. In some embodiments, there is a mechanism in the sleeve 9 for releasing or connecting the surgical appliance 36 in the base 10, for example: a button or a lever, according to another embodiment of the invention.

In this example the cannulas 14 are adapted to connect a surgical appliance 36 inside the surgical site 26. In some embodiment, the cannulas 14 including the beater 27 which both serves to prevent the protector guide 8 from slipping out of the cannulas 14 and to connect a surgical appliance 36 to the cannula 14. In some embodiments, the fitting 30 connect a surgical appliance 36 to the cannula 14. In some examples, at least, one of said plurality of cannulas 14 is adapted to connect, at least, a surgical appliance 36 in the surgical site 26. In some embodiments, the connection of the surgical appliance 36 to the cannula 14 is made by friction, in some embodiments, the connection of the surgical appliance 36 to the cannula 14 is made by electrical connection, in some embodiments, the connection of the surgical appliance 36 to the cannula 14 is made by mechanical connection, but the type of connection is not limited to them. In some embodiments, the surgical appliances 36 that connect the distal end of the cannula 14 are: a hose, a cannula, a surgical instrument, part of a surgical instrument, a surgical drain, a surgical camera, an electronic appliance, a mechanical appliance, but it is not limited to them. In some embodiments here is a mechanism in the sleeve 9 for releasing or connecting the surgical appliance 36 in the cannula 14, for example: a button or a lever. In some embodiments, the fixation is not limited to single cannula 14. In some embodiments, the surgical appliance 36 is connected to at least one of the plurality of cannulas 14 in the surgical site 26 after the trocar 34 is punctured in the tissue 25, according to another embodiment of the invention.

Generally, after the surgery, the trocar 34 is removed from the tissue 25, the surgeon pulls the sleeve 9 out of the tissue 25, according to another embodiment of the invention.

It will be apparent to one skilled in the art that the invention may be provided including some or all the mentioned features and components without departing from the spirit and scope of the invention. For purposes of comparing some embodiments, certain aspects and advantages of these embodiments are described. Not necessarily all such aspects or advantages are achieved by any particular embodiment. Thus, for example, some embodiments can be carried out in a manner that achieves or optimizes one advantage or group of advantages as described, herein without necessarily achieving other aspects or advantages as can also be described or suggested herein. It will also be apparent to the skilled artisan that the embodiments described above are specific examples of a broader invention which may have greater scope than any of the singular descriptions taught. There may be many alterations made in the descriptions without departing from the spirit scope of the invention. Although, certain preferred embodiments and examples are disclosed, inventive subject matter extends beyond the specifically disclosed embodiments to other alternative embodiments and/or uses, and to modifications and equivalents thereof. Thus, the scope of the claims appended hereto is not limited by any of the particular embodiments described. For example, in any method or process disclosed herein, the acts or operations of the method or process can be performed in any suitable sequence, and they are not necessarily limited to any particular disclosed sequence. Some operations can be described as multiple discrete operations in turn, in a manner that can be helpful in understanding certain embodiments, however, the order of description should not be construed to imply that these operations are order dependent.

I claim:

1. A trocar (34) for transfixing a plurality of cannulas (14) through a tissue (25) for providing a plurality of entry-ports (33) to a surgical site (26), comprising: a base (10) and a plurality of cannulas (14) connected to said base (10), wherein said cannulas (14) include an access-port (3); the trocar further comprising a mandrel (1) including a handle (7), said mandrel (1) including a plurality of piercing tips (2) connected to said handle (7), wherein said mandrel (1) detachably engages the trocar (34) forming a single punch assembly.

2. The trocar of claim 1, wherein said plurality of cannulas (14) include a dilator (11).

3. The trocar of claim 1, wherein at least one of said cannulas (14) further comprise a distal sharp tip (32) to transfix the tissue (25).

4. A trocar (34) for transfixing a plurality of cannulas (14) through a tissue (25) for providing a plurality of entry-ports (33) to a surgical site (26), comprising: a sleeve (9) including a base (10); said sleeve (9) including a plurality of cannulas (14) connected to said base (10); a mandrel (1) including a handle (7); and said mandrel (1) including a plurality of piercing tips (2) connected to said handle (7); wherein said mandrel (1) detachably engages said sleeve (9) forming a single punch assembly; wherein said cannulas (14) include an access-port (3).

5. The trocar of claim 4, wherein said plurality of cannulas (14) have an outer diameter adapted to cause minimal trauma to the tissue (25) to prevent scar.

6. The trocar of claim 4, wherein said plurality of cannulas (14) comprise a distal end adapted to dilate said tissue (25) entry-port (33) to prevent scar.

7. The trocar of claim 4, wherein at least one of said plurality of piercing tips (2) comprise a retractable protection system (37).

8. The trocar of claim 4, wherein said cannulas (14) comprise a coil (21) which keeps open the access-port (3).

9. The trocar of claim 4, wherein said cannula (14) comprises a fastening system (35) configured to fasten tissue (25).

10. The trocar of claim 4, wherein at least one part is made in a transparent material.

11. The trocar of claim 4, further comprising a male-female connection (38).

12. The trocar of claim 4, further comprising a faucet (12) to control an access of liquids and gases to a surgical site (26).

13. The trocar of claim 4, further comprising a valve (13) to prevent escaping of gas and liquid from said surgical site (26).

14. The trocar of claim 4, further comprising a protector guide (8) to drive and protect the piercing tip (2).

15. The trocar of claim 4, wherein said base (10) is adapted to connect to a surgical appliance (36).

16. The trocar of claim 4, wherein at least one of said plurality of cannulas (14) is adapted to connect a surgical appliance (36) within the surgical site (26).

17. A method for providing a plurality of entry-ports (33) through tissue (25) to a surgical site (26), comprising: (a) transfixing a plurality of cannulas (14) of a trocar (34) in a tissue (25), (b) using at least one said cannula (14) as an access-port (3) for said surgical site (26), (c) removing said trocar (34) from said tissue (26), and (d) attaching a mandrel (1) including a plurality of piercing tips (2) within a sleeve (9) including a plurality of cannulas (14).

18. The method of claim 17, further comprising: (e) connecting a surgical appliance (36) to the trocar (34).

* * * * *